(12) United States Patent
Gross et al.

(10) Patent No.: US 11,628,127 B2
(45) Date of Patent: Apr. 18, 2023

(54) COMPOSITION FOR LIGHTENING OR DYEING KERATIN FIBERS WITH A LOW AMOUNT OF OXIDIZING AGENT

(71) Applicant: Noxell Corporation, Hunt Valley, MD (US)

(72) Inventors: Andrej Gross, Darmstadt (DE); Bjoern Hoffmann, Darmstadt (DE); Simon Paul Godfrey, Oberursel (DE); Lina Makavou-Jennen, Darmstadt (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/327,707

(22) PCT Filed: Sep. 14, 2017

(86) PCT No.: PCT/US2017/051632
§ 371 (c)(1),
(2) Date: Feb. 22, 2019

(87) PCT Pub. No.: WO2018/053177
PCT Pub. Date: Mar. 22, 2018

(65) Prior Publication Data
US 2019/0224088 A1 Jul. 25, 2019

(30) Foreign Application Priority Data
Sep. 14, 2016 (EP) ..................... 16188777

(51) Int. Cl.
| | | |
|---|---|---|
| *A61K 8/34* | (2006.01) | |
| *A61Q 5/08* | (2006.01) | |
| *A61K 8/22* | (2006.01) | |
| *A61K 8/31* | (2006.01) | |
| *A61Q 5/10* | (2006.01) | |
| *A61K 8/41* | (2006.01) | |

(52) U.S. Cl.
CPC ............... *A61K 8/22* (2013.01); *A61K 8/31* (2013.01); *A61K 8/342* (2013.01); *A61K 8/41* (2013.01); *A61Q 5/08* (2013.01); *A61Q 5/10* (2013.01); *A61K 2800/30* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 8,142,518 B2 * | 3/2012 | Deconinck | ............... | A61K 8/31 8/405 |
| 8,444,712 B2 * | 5/2013 | Lim | .................... | A61K 8/494 8/405 |
| 9,687,057 B2 * | 6/2017 | Mignon | .................. | A61K 8/31 |

FOREIGN PATENT DOCUMENTS

| | | | | |
|---|---|---|---|---|
| JP | 2008074712 A | | 4/2008 | |
| WO | WO-02074272 A1 * | | 9/2002 | ............... A61K 8/44 |
| WO | WO-2011076646 A2 | | 6/2011 | |
| WO | WO-2012146529 A1 | | 11/2012 | |
| WO | WO-2013079527 A1 * | | 6/2013 | ............... A61K 8/31 |
| WO | WO-2013079527 A1 | | 6/2013 | |
| WO | WO-2014020146 A1 | | 2/2014 | |
| WO | WO-2014020146 A2 | | 2/2014 | |
| WO | WO-2018053177 A1 | | 3/2018 | |

OTHER PUBLICATIONS

"European Application Serial No. 16188777.3, Communication Pursuant to Article 94(3) EPC dated Jan. 24, 2019", 7 pgs.
"European Application Serial No. 16188777.3, Extended European Search Report dated Dec. 23, 2016", 10 pgs.
"European Application Serial No. 16188777.3, Response filed Aug. 30, 2018 to Extended European Search Report dated Dec. 23, 2016", w/ English Claims, 15 pgs.
"International Application Serial No. PCT/US2017/051632, International Search Report dated Nov. 3, 2017", 6 pgs.
"International Application Serial No. PCT/US2017/051632, Written Opinion dated Nov. 3, 2017", 8 pgs.
"European Application Serial No. 16188777.3, Communication Pursuant to Article 94(3) EPC dated Oct. 2, 2019", 5 pgs.
"European Application Serial No. 16188777.3, Response Filed Jul. 30, 2019 to Communication Pursuant to Article 94(3) EPC dated Jan. 24, 2019", 31 pgs.
"International Application Serial No. PCT/US2017/051632, International Preliminary Report on Patentability dated Mar. 28, 2019", 10 pgs.

\* cited by examiner

*Primary Examiner* — Celeste A Roney
(74) *Attorney, Agent, or Firm* — Dennemeyer & Associates LLC; Victoria Friedman

(57) ABSTRACT

Composition for lightening keratin fibers, comprising: at least 20% weight of fatty substances free of carboxylic acid groups relative to the total weight of the composition, at least one alkalizing agent, at least one surfactant, and at least one oxidizing agent, wherein the concentration of oxidizing agent in the composition is from 1.5% to 2.5% by weight relative to the total weight of the composition.

9 Claims, No Drawings

COMPOSITION FOR LIGHTENING OR DYEING KERATIN FIBERS WITH A LOW AMOUNT OF OXIDIZING AGENT

PRIORITY

This application is a U.S. National Stage Filing under 35 U.S.C. 371 from International Application No. PCT/US2017/051632, filed on Sep. 14, 2017, and published as WO 2018/053177 on Mar. 22, 2018, which application claims the benefit of priority from EP Patent Application No. 16188777.3, filed on Sep. 14, 2016, which are herein incorporated in their entirety by reference.

FIELD OF THE INVENTION

The invention provides compositions for lightening or dyeing keratin fibers, in particular human keratin fibers such as the hair, comprising a high concentration of fatty substances and a low concentration of oxidizing agent.

BACKGROUND OF THE INVENTION

The permanent alteration of the hair color by the application of hair dyes is well known. In order to provide the consumer with the shade and the intensity of the desired color, a complex chemical process is utilized. Permanent hair dyeing formulations typically comprise oxidative hair dye precursors, which can diffuse into the hair through the cuticle and into the cortex where they then react with each other and a suitable oxidizing agent to form the final dye molecules. Due to their larger size, the resultant molecules are unable to readily diffuse out of the hair during subsequent washing with water and/or detergents; hence delivering a consumer-desired permanency of color. This reaction typically takes place in an aggressive environment at approximately pH 10 in the presence of an alkalizing agent and an oxidizing agent. Typically an oxidizing composition comprising the oxidizing agent and a dye composition comprising the alkalizing agent and if present the oxidative dye precursor(s) are mixed shortly before use. The consumer repeats this process regularly in order to maintain the desired hair color and shade and the intensity of color and to ensure continual, even coverage of the hair including coverage of new hair growth.

Hair dyeing involves the application of one or more oxidative dye precursor(s) onto hair which results in the coloration of hair fibers, Hair color may be changed subtly or dramatically, the root growth colored to match the remaining head of hair, effects introduced such as glitter, hair swatch effects or other sectional effects, or the same color "freshened up" to combat fade and/or wash-out. In modern times, the consumer has a wide variety of options for dyeing the hair (whether in the salon or at home) from direct dyes that wash out relatively quickly, hair make-up for applying glitter and/or hair swatch effects, to conventional (semi-) permanent dyeing technology.

Alternatively, when a person wishes to drastically change hair color, in particular when they wish to obtain a lighter color than the original color, it is often necessary to use higher levels of oxidizing agents in order to be able to effectively lighten the melanin within hair to enable the user to get the desired color result.

It is known to lighten keratin fibers, in particular human keratin fibers such as the hair, with lightening compositions containing one or more oxidizing agents. The role of this oxidizing agent is to break down the melanin of hair, which, depending on the nature of the oxidizing agent present, results in a more or less pronounced lightening of the fibers. Typically for drastically change colors, the stylist or retail consumer will be forced to choose oxidizing compositions which utilise the higher levels of oxidizing agents.

It is particularly important to have simultaneous hair lightening and dyeing in compositions which deliver permanent hair color. There are two main distinctions in the result obtained versus semi-permanent color. The permanent products are designed to give longer lasting colors, and also to be able to cover higher degrees of grey hairs. They achieve this by at least in part having the ability to lighten the underlying pigmented hair to a higher degree. This reduces the color difference in the underlying hair between the pigmented and grey hair, and facilitates the role of the dyes to then deliver a higher degree of grey coverage. Permanent dyeing compositions which are applied to the hair, as known by those skilled in the art, will typically contain around 3% by weight of the final composition of oxidizing agent for providing brown and darker shades, whereas those that are used applied to provide blonde shades typically have at least 4.5% by weight of the final composition of oxidizing agent.

Many attempts have been made in the field of hair dyeing or of lightening compositions in order to improve the dyeing properties and the lightening properties.

To obtain a product for lightening or dyeing keratin fibers which is more effective in terms of dyeing and lightening properties, it is known to use a substantial amount of one or more fatty substances such as oils in a lightening or dyeing composition.

However, while a high concentration of oxidizing agent can provide the desired increase in degree of hair lightening, it also leads to an undesired increase in degree of degradation of the keratin fibers. Thereby, the introduction of a large amount of oil, in replacement of water in a lightening or dyeing formulation proves to be problematic in terms of damages on the hair. Indeed, the concentration of oxidizing agent is increased in the aqueous oxidizing composition.

Thus, there is a need to have satisfactory efficacy for hair lightening products and for hair dyeing products, especially in terms of lightening properties, providing sufficient hair lightening while at the same time reducing the degradation of the keratin fibers.

SUMMARY OF THE INVENTION

The inventors have surprisingly found that these needs can be met by the composition for lightening or dyeing keratin fibers according to the present invention, wherein the concentration of oxidizing agent is lower than the concentration usually used in compositions known in the art.

While a composition with a high oil concentration can cause degradation of the keratin fibers, the composition for lightening or dyeing keratin fibers according to the present invention presents good lightening properties with low damages on the keratin fibers.

The present invention relates to a composition for lightening keratin fibers, comprising:
at least 20% by weight of fatty substances free of carboxylic acid groups relative to the total weight of the composition,
at least one alkalizing agent,
at least one surfactant, and
at least one oxidizing agent, wherein the concentration of oxidizing agent in the composition is from 1.5% to 2.5% by weight relative to the total weight of the composition.

The present invention further relates to a composition for dyeing keratin fibers, comprising:
- at least 20% by weight of fatty substances free of carboxylic acid groups relative to the total weight of the composition,
- at least one alkalizing agent,
- at least one surfactant,
- at least two oxidative dye precursors comprising one or more primary intermediates and one or more couplers, and
- at least one oxidizing agent, wherein the concentration of oxidizing agent in the composition is from 1.5% to 2.5% by weight relative to the total weight of the composition, wherein the total concentration of primary intermediates in the composition is more than 10 mM/kg of the composition and wherein the color result of the composition has an L* value of less than 40 on natural white hair according to the L*a*b system.

Such compositions can achieve the desired hair lightening, i.e. deliver brown/dark permanent hair colors, with a low concentration of oxidizing agent while limiting the degradation of the keratin fibers.

The present invention further relates to a composition for dyeing keratin fibers, comprising:
- at least 20% by weight of fatty substances free of carboxylic acid groups relative to the total weight of the composition,
- at least one alkalizing agent,
- at least one surfactant,
- at least two oxidative dye precursors comprising one or more primary intermediates and one or more couplers, and
- at least one oxidizing agent, wherein the concentration of oxidizing agent in the composition is from 2.6% to 4% by weight relative to the total weight of the composition, wherein the total concentration of primary intermediates in the composition is equal to or less than 10 mM/kg of the composition and wherein the color result of the composition has an L* value greater than or equal to 40 on natural white hair according to the L*a*b system.

This composition can achieve the desired hair lightening, i.e. deliver blonde permanent hair colors, with a low concentration of oxidizing agent. This composition presents low damages on the keratin fibers.

A composition for lightening keratin fibers comprises at least 20% by weight of fatty substances free of carboxylic acid groups relative to the total weight of the composition, and at least one oxidizing agent. The concentration of oxidizing agent in the composition is from 1.5% to 2.5% by weight relative to the total weight of the composition.

A composition for dyeing keratin fibers further comprises at least two oxidative dye precursors comprising one or more primary intermediates and one or more couplers and at least one oxidizing agent. The concentration of oxidizing agent in the composition is from 1.5% to 2.5% by weight relative to the total weight of the composition. The color result of the composition has an L* value of less than 40 on natural white hair according to the L*a*b system.

A composition for dyeing keratin fibers further comprises a concentration of oxidizing agent in the composition from 2.6% to 4% by weight relative to the total weight of the composition. The color result of the composition has an L* value greater than or equal to 40 on natural white hair according to the L*a*b system.

The present invention also relates to a process for lightening or dyeing keratin fibers, comprising the application of one of the compositions as defined hereinbefore.

Another subject of the invention relates to kit for lightening or dyeing keratin fibers comprising a first compartment containing a first composition comprising at least one fatty substance free of carboxylic acid groups, at least one alkalizing agent, optionally at least two oxidative dye precursors comprising one or more primary intermediates and one or more couplers, and in a second compartment, a second composition comprising at least one oxidizing agent. The compositions of the two compartments are intended to be mixed in order to provide the composition according to the invention, before application on to keratin fibers.

The invention lastly relates to kit for lightening or dyeing keratin fibers comprising a first compartment containing a first composition comprising at least one fatty substance free of carboxylic acid groups, in a second compartment, a second composition comprising at least one alkalizing agent, optionally at least two oxidative dye precursors comprising one or more primary intermediates and one or more couplers, and in a third compartment, a third composition comprising at least one oxidizing agent. The compositions of the three compartments are intended to be mixed in order to provide the composition according to the invention, before application on to keratin fibers.

DETAILED DESCRIPTION OF THE INVENTION

Definitions

In this document, including in all embodiments of all aspects of the present invention, the following definitions apply unless specifically stated otherwise.

The term "hair" as used herein means mammalian hair including scalp hair, facial hair and body hair, more preferably hair on the human head and scalp. Hair comprises hair fibers. As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

The human keratin fibers treated via the compositions according to the invention are preferably hair.

The term "damage" as used herein refers to changes in the chemical and physical structure of human hair after it emerges from the follicle due to the hair lightening and dyeing process. While hair is naturally subjected to wear and tear in the process of normal grooming, the process of lightening and dyeing hair leads to additional damage mechanisms. Such processes use hydrogen peroxide at an alkali pH, which can lead to both oxidation and radical induced damage to hair proteins and lipids. These may in turn lead to higher levels of mechanical damage during normal grooming, as the hair itself is weakened by the oxidative and radical modifications. One way to assess the level of chemical damage is to monitor the level of cysteic acid formed by the oxidation of disulphide bonds during the hair lightening and dyeing process. Fourier Transform Infrared spectroscopy (FTIR) using an Attenuated Total Reflectance (ATR) system is a useful way to probe such chemical differences. (Signori C, Lewis D M, *Macromol. Symp.*, 119 (1997), pp. 240-253, Signori C, Lewis D M, Int. *J. Cosmet. Sci.*, 19 (1997), pp. 1-13).

The term "lightening" as used herein refers to changes in the appearance of the hair strands. More specifically it refers to changes to the melanin, the hairs natural pigment, and the ability to reduce the total hair strands melanin light absorbing properties. When this occurs, the hair, when dry, looks lighter in color than before the product was applied.

The term "comprising" means that other steps and other ingredients can be added. "Comprising" encompasses the terms "consisting of" and "consisting essentially of".

The term "derivatives" as used herein includes but is not limited to: ester, amide, carboxyl, amino, ether, acetyl, acid, their salts and/or their alcohol or hydroxy derivatives of a given compound.

The term "molecular weight of a polymer" or "M.Wt. of a polymer" as used herein refers to the weight average molecular weight unless otherwise stated. The weight average molecular weight may be measured by gel permeation chromatography.

The term "cosmetically acceptable salt" as used herein refers to conventional base-addition salts that retain the properties of the one or more acrylic compounds of the present invention and are formed from suitable organic or inorganic bases. Sample base-addition salts include those derived from sodium, potassium, ammonium, calcium, magnesium, iron, zinc, zirconium and aluminium hydroxide. Chemical modification of a compound bearing a carboxylic acid function into the corresponding carboxylate salt is a technique well known in the art.

All percentages are by total weight (w/w) of the composition, unless otherwise specified. All ratios are weight ratios. "% wt." means percentage by weight. References to 'parts' e.g. a mixture of 1 part X and 3 parts Y, is a ratio by weight.

The term "kit" as used herein means a packaging unit comprising a plurality of compartments i.e. a kit of parts. An example of a kit is, for example, a first composition and a separately packaged second composition. Another kit may comprise application instructions comprising a method and a composition/formulation.

Description of the Invention

The compositions for lightening keratin fibers or for dyeing keratin fibers may be inverse emulsions (water-in-oil). It is known in the art that an emulsion comprises a dispersed phase and a continuous phase. Inverse emulsion is understood to mean an emulsion containing a dispersed aqueous phase and a continuous oil phase.

The composition may be in various forms, such as in the form of liquids, milks or crème, or in any other form that is suitable for lightening or dyeing keratin fibers, and especially human hair.

Preferably, the composition is in the form of a milk or a crème.

When the composition according to the invention is used for lightening, it does not comprise an oxidation dye precursor or a direct dye that are normally used for dyeing keratin fibers. If it does comprise any, the total content of oxidation dye precursor or of direct dye does not exceed 0.005% by weight relative to the weight of the composition.

Fatty Substances

According to the invention, the dyeing or lightening composition comprises at least 20% by weight of fatty substances free of carboxylic acid groups relative to the total weight of the composition.

Preferably, the composition comprises no fatty substances with carboxylic acid groups.

The term "fatty substance" means an organic compound that is an insoluble organic in water at room temperature (25° C.) and at atmospheric pressure (760 mmHg) (solubility of less than 5%, preferably 1% and more preferably still 0.1%). In addition, under the same temperature and pressure conditions, the fatty substances are soluble in organic solvents such as chloroform, ethanol or benzene, for example.

The term "fatty substance free of carboxylic acid groups" means fatty substance containing no —COOH groups and no —COO groups.

Preferably, the fatty substances of the invention are selected from the group consisting of liquid hydrocarbons, non-silicone oils of animal, plant, mineral or synthetic origin, liquid fatty alcohols, liquid fatty esters, silicones and fatty ethers, or mixtures thereof.

The fatty substances of the invention may be liquid or non-liquid at room temperature (25° C.) and at atmospheric pressure (760 mmHg; i.e. $1.013 \times 10^5$ Pa). The liquid fatty substances of the invention preferably have a viscosity of less than or equal to 2 Pa·s, better less than or equal to 1 Pa·s and even better less than or equal to 0.1 Pa·s at a temperature of 25° C. and at a shear rate of 1 $s^{-1}$. The term "liquid hydrocarbon" means a hydrocarbon composed solely of carbon and hydrogen atoms, which is liquid at ordinary temperature (25° C.) and at atmospheric pressure (760 mmHg; i.e. $1.013 \times 10^5$ Pa).

More particularly, the liquid hydrocarbons are chosen from:

- linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

Preferably, the liquid hydrocarbon(s) is (are) chosen from volatile or non-volatile liquid paraffins, and liquid petroleum jelly. Preferably, the liquid hydrocarbon is liquid petroleum jelly.

The term "liquid fatty alcohol" means a non-glycerolated and non-oxyalkylenated fatty alcohol that is liquid at room temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated. The saturated liquid fatty alcohols are preferably branched. They may optionally comprise in their structure at least one aromatic or non-aromatic ring. They are preferably acyclic.

More particularly, the liquid saturated fatty alcohols of the invention are chosen from octyldodecanol, isostearyl alcohol, 2-hexyldecanol and mixtures thereof. Preferably, the liquid saturated fatty alcohol of the invention is octyldodecanol.

These liquid unsaturated fatty alcohols have at least one double or triple bond. Preferably, the fatty alcohols of the invention bear in their structure one or more double bonds. When several double bonds are present, there are preferably 2 or 3 of them, and they may be conjugated or non-conjugated. These unsaturated fatty alcohols may be linear or branched. They may optionally comprise in their structure at least one aromatic or non-aromatic ring. They are preferably acyclic.

More particularly, the liquid unsaturated fatty alcohols of the invention are chosen from oleyl alcohol, linoleyl alcohol, linolenyl alcohol, undecylenyl alcohol and mixtures thereof.

The term "liquid fatty ester" means an ester derived from a fatty acid and/or from a fatty alcohol and that is liquid at room temperature (25° C.) and at atmospheric pressure (760 mmHg; i.e. $1.013 \times 10^5$ Pa).

The esters are preferably liquid esters of saturated or unsaturated, linear or branched. $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

Composition according to the invention may also comprise, as liquid fatty ester, sugar esters and diesters of $C_6$-$C_{30}$ and preferably $C_{12}$-$C_{22}$ fatty acids. The ter it "sugar" means oxygen-bearing hydrocarbon-based compounds which contain several alcohol functions, with or without aldehyde or ketone functions, and which comprise at least 4 carbon atoms. These sugars may be monosaccharides, oligosaccharides or polysaccharides.

Examples of suitable sugars include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, nesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

Monoesters and diesters and especially sucrose, glucose or methylglucose monooleates or dioleates, stearates, behenates, oleopalmitates, linoleates, linolenates and oleostearates are more particularly used.

Finally, natural or synthetic esters of monoacids, diacids or triacids with glycerol may also be used.

Among these are plant oils. As oils of plant origin or synthetic triglycerides that may be used in the composition of the invention as liquid fatty esters, examples include:

triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, jojoba oil and rhea butter oil.

The term "liquid silicone" means an organopolysiloxane that is liquid at room temperature (25° C.) and at atmospheric pressure (760 mmHg; i.e. $1.013 \times 10^5$ Pa).

Preferably, the silicone is chosen from liquid polydialkylsiloxartes, especially liquid polydimethylsiloxanes (PDMSs) and liquid polyorganosiloxanes comprising at least one aryl group.

These silicones may also be organomodified. The organomodified silicones that can be used are liquid silicones as defined above and comprising in their structure one or more organofunctional groups attached via a hydrocarbon-based group. They may be volatile or non-volatile. When they are volatile, the silicones are more particularly chosen from those having a boiling point of between 60° C. and 260° C., and more particularly still from:

(i) cyclic polydialkylsiloxanes comprising from 3 to 7 and preferably 4 to 5 silicon atoms;

(ii) linear volatile polydialkylsiloxanes containing 2 to 9 silicon atoms and having a viscosity of less than or equal to $5 \times 10^{-6}$ m$^2$/s at 25° C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups. There is also polydimethylstioxanes containing dimethylsilanol end groups known under the name Dimethiconol (CTFA).

The organomodified liquid silicones may especially con a n poly ethyleneoxy and/or polypropyleneoxy groups.

Composition according to the invention may also comprise non-liquid fatty substances at room temperature and at atmospheric pressure.

The term "non-liquid" preferably means a solid compound or a compound that has a viscosity of greater than 2 Pa·s at a temperature of 25° C. and at a shear rate of 1 s$^{-1}$.

More particularly, the non-liquid fatty substances are chosen from fatty alcohols, esters of fatty acids and/or of fatty alcohols, non-silicone waxes, silicones and fatty ethers, which are non-liquid and preferably solid.

The non-liquid fatty alcohols may be chosen from saturated or unsaturated, linear or branched alcohols comprising from 8 to 30 carbon atoms, for example, of cetyl alcohol, stearyl alcohol and a mixture thereof (such as cetylstearyl alcohol).

Preferably, the non-liquid fatty alcohol of the invention is cetylstearyl alcohol.

As regards the non-liquid esters of fatty acids and/or of fatty alcohols, there is especially of solid esters derived from $C_9$-$C_{26}$ fatty acids and from $C_9$-$C_{26}$ fatty alcohols. Among these esters, mention may be made of octyldodecyl behenate; isocetyl behenate; cetyl lactate; stearyl octanoate, octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used. There is also diethyl sebacate; diisopropyl sebacate; diisopropyl adipate; di-n-propyl adipate; dioctyl adipate, dioctyl maleate.

Among all the additional esters mentioned above, it is preferred to use myristyl, cetyl or stearyl palmitates, alkyl myristates such as cetyl myristate, and stearyl myristyl myristate.

The (non-silicone) wax(es) may be selected from carnauba wax, candelilla wax, esparto grass wax, paraffin wax, ozokerite, plant waxes such as olive wax, rice wax, hydrogenated jojoba wax or the absolute waxes of flowers, animal waxes, for instance beeswaxes or modified beeswaxes (cerabellina).

Composition according to the invention may comprise non-liquid silicones in the form of waxes, resins or gums.

The non-liquid silicone may be chosen from polydialkylsiloxanes, especially polydimethylsiloxanes (PDMS), and organomodified polysiloxanes comprising at least one functional group chosen from poly(oxyalkylene) groups, amino groups and alkoxy groups.

The silicone gums are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

The non-liquid fatty ethers may be chosen from dialkyl ethers and especially dicetyl ether and distearyl ether, alone or as a mixture.

Preferably, the fatty substances used in the composition according to the invention do not comprise any oxyalkylene units or any glycerol units.

Preferably, the fatty substances free of carboxylic acid groups used in the composition are selected from the group consisting of liquid paraffins, liquid petroleum jelly, polydecenes, liquid fatty acid esters, liquid fatty alcohols such as octyldodecanol or non-liquid fatty alcohols such as cetylstearyl alcohol, and mixtures thereof.

More preferably, the fatty substances free of carboxylic acid groups are selected from the group consisting of liquid petroleum jelly, liquid fatty alcohols such as octyldodecanol or non-liquid fatty alcohols such as cetylstearyl alcohol, and mixtures thereof.

Preferably, the composition according to the invention contains one or more fatty substances that are liquid at room temperature (25° C.) and at atmospheric pressure (760 mmHg; i.e. $1.013 \times 10^5$ Pa), optionally combined with one or more fatty substances that are non-liquid under the same conditions.

The composition according to the invention comprises an amount of fatty substances free of carboxylic acid groups of at least 25%, preferably of at least 30%, more preferably of at least 40% by total weight of the composition.

Preferably, the concentration of fatty substances free of carboxylic acid groups ranges from 25% to 85%, more preferably from 25% to 60%, even more preferably from 30% to 55% by total weight of the composition.

Alkalizing Agents

The composition according to the present invention comprises at least one alkalizing agents.

By "alkalising agent", it is meant one or more compounds suitable for increasing the pH to alkaline levels. That is to say, the alkalising agent(s) is (are) generally such that the $pK_b$ at 25° C. is less than 12, preferably less than 10 and more advantageously less than 6. Generally, the most commonly used alkalising agent in the art is ammonia. Non-ammonia alkalising agents are also known and advantageous in view of reduced olfactory stimulation, e.g. alkanolamines.

Suitable alkalizing agents include, but are not limited to: ammonia; alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The composition of the invention may comprise one or more non-ammonia alkalizing agents selected from the group consisting of: monoethanolamine (MEA), sodium silicate, sodium meta silicate, diethanolamine, triethanolamine, monopropanolamine, dipropartolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol, and mixtures thereof.

Monoethanolamine (MEA) or aminomethylpropanol (AMP) are commonly used in ammonia-free hair dye products.

Preferably, the alkalising agent is monoethanolamine (MEA) alone or in combination with other alkalizing agents.

Monoethanolamine may in particular be preferred to be used alone or in combination with other non-ammonia alkalising agent.

The composition according to the invention preferably does not comprise any aqueous ammonia or salts thereof as alkalising agent. If however, it did comprise any, its content would not exceed 0.03% by weight, preferably not exceed 0.01% by weight relative to the weight of the composition of the invention.

Preferably, if the composition comprises aqueous ammonia or a salt thereof, then the amount of non-ammonia alkalising agent is greater than the amount of aqueous ammonia.

The composition may comprise an alkalising agent which is monoethanolamine (MEA) and a primary intermediate which is 2-methoxymethyl-1,4-benzenediamine.

The composition of the invention may comprise a total amount of alkalizing agents ranging from 0.01% to 10%, preferably from 0.1% to 8%, more preferably from 0.1% to 5% by total weight of the composition.

The composition of the invention may comprise a total amount of alkalizing agents of less than 10%, preferably less than 8%, more preferably less than 5% by total weight of the composition.

Oxidative Dye/Direct Dye

The composition of the invention may optionally comprise at least one dye chosen from oxidative dyes precursors, direct dyes or mixture thereof.

The composition of the invention may comprise at least one oxidative dye precursor, which are usually classified, either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Preferably, the composition of the invention comprises at least two oxidative dye precursors comprising one or more primary intermediates and one or more couplers.

The oxidative dye precursors suitable for use herein, in so far as they are bases, may be used as free bases or in the form of any cosmetically acceptable salts obtained with the corresponding organic or inorganic acids, such as hydrochloric, hydrobromic, citric, acetic, lactic, succinic, tartaric, or sulfuric acids, or, in so far as they have aromatic hydroxyl groups, in the form of any cosmetically acceptable salts obtained with the corresponding bases, such as alkali phenolates.

Oxidative dye precursors are known in the art, and include aromatic diamines, aminophenols, aromatic diols and their derivatives (a representative but not exhaustive list of oxidation dye precursors can be found in Sagarin, "Cosmetic Science and Technology", Interscience, Special Edn. Vol. 2 pages 308 to 310). Suitable oxidative dye precursors are also disclosed in the Canadian Patent Application No. CA2576189A1—in particular, from Table 1 dye combinations No. 1 to 2394, which span pages 49 to 238, are incorporated herein by reference. It is to be understood that the one or more primary intermediates and the one or more couplers (collectively known as oxidative dye precursors) detailed below are only by way of example and are not intended to limit the compositions and other aspects herein described. The one or more primary intermediates and the one or more couplers may be used in the form of any cosmetically acceptable salts, for example sulfate salts.

The one or more primary intermediates may be selected from the group consisting of toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexlpyrazole, 4,5-diamino-1-heptylpyrazole, methoxymethyl-1,4-diaminobenzene, N,N-bis(2-hydroxy ethyl)-N-(4-aminophenyl)-1,2-diaminothane, 2-[(3-aminopyrazolo[1,5-a]pyridin-2-yl)oxy]ethanol hydrochloride, their salts thereof and mixtures thereof.

The one or more primary intermediate of the composition may be particularly 1,4-diamino-2-(methoxymethyl)-benzene. 1,4-diamino-2-(methoxymethyl)-benzene has the advantage of an improved sensitisation profile (i.e. reduced risks of scalp skin reaction).

The one or more primary intermediate may be 4,5-diamino-1-hexylpyrazole, 4,5-diamino-1-hexylpyrazole used as a sulfate salt.

The one or more primary intermediate may be selected from the group consisting of 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, and mixtures thereof; and the cosmetically acceptable salts thereof such as chlorides, sulfates and hemi-sulfates in particular.

The one or more couplers may be a compound comprising one or more phenyl rings substituted with one or more hydroxyl groups.

The one or more couplers may be selected from the group consisting of resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxy ethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The oxidative dye precursors may be particularly selected from the group consisting of 1-naphthol, 2,4-diaminophenoxyethanol, toluene-2,5-diamine sulfate, resorcinol, 4-amino-m-cresol, 2-amino-4-hydroxyethylaminoanisole sulfate, N,N-bis(2-hydroxyethyl)-p-phenylenediamine, hydroxyethyl-3,4-methylenedioxyaniline HCl, 1-hydroxyethyl 4,5-diamino pyrazole sulfate, 4-amino-2-hydroxytoluene, p-aminophenol, 2-methoxymethyl-p-phenylenediamine 2-methylresorcinol, m-aminophenol, 2-methyl-5-hydroxyethylaminophenol, and mixtures thereof.

Preferably, the primary in ciliates are selected from the group consisting of toluene-2,5-diamine, 2-methoxymethyl-p-phenylenediamine, N,N-bis(2-hydroxyethyl)-p-phenylenediamine, p-aminophenol and mixtures thereof.

Preferably, the couplers are selected from the group consisting of resorcinol, methyl-resorcinol, naphthol, m-aminophenol, 4-amino-2-hydroxytoluene, 2-methyl-5-hydroxyethylaminophenol, 2,4-diaminophenoxyethanol, 2-amino-4-hydroxyethylaminoanisole and mixtures thereof.

The composition according to the present invention may further comprise compatible direct dyes, in an amount sufficient to provide additional colouring, particularly with regard to intensity. The composition may further comprise one or more direct dyes, advantageously one or more oxidatively stable direct dyes.

Typically, compositions of the invention may comprise a total amount of direct dyes ranging from 0.001% to 1%, preferably from 0.005% to 0.5%, more preferably from 0.01% to 0.25%, by total weight of the composition.

The presence of one or more direct dyes and the proportion thereof can help to provide or enhance coloring/dyeing, particularly with regard to the vibrancy of the color that is desired.

Preferably, the composition of the invention is substantially free of any direct dyes. Indeed, sometimes consumers prefer direct dye-free compositions.

The one or more direct dyes may be selected from the group consisting of nitro dyes to provide a blue color, nitro dyes to provide a red color or a yellow color, quinone dyes, basic dyes, neutral azo dyes, acid dyes, and mixtures thereof. The one or more direct dyes may be a basic dye. The one or more direct dyes may be a neutral azo dye. The one or more direct dyes may be an acid dye.

The one or more direct dyes may be selected from the group consisting of Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-diaxo-9,10-dihydroanthracen-1-ylamino)propyl)-4-methylmorpholin-4-ium-methysulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, 2-amino-6-chloro-4-nitrophenol, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

The level of oxidative dye precursors used in the composition of the invention is described herein with reference to the level of primary intermediates within the composition. This proves a useful reference, as it's generally considered that the level of primary intermediates dictates the level of color formed. Whilst not wishing to be bound to theory, it's believed that the rate limiting step during color formation is the oxidation of the primary intermediate, with the subsequent coupling reactions occurring rapidly. As the primary intermediates have different chemical structures, and for some the primary intermediate is also available either as pure materials or in the form of various salts, it's not practical to consider the amount of primary intermediate simply in terms of weight added to the composition. The following expression is used to calculate the level of primary intermediates within the composition such that it's expressed in terms of molar concentrations.

$$\text{mM dyes/Kg composition} = 1000 * \sum_{n=1}^{n=n} \frac{10*(\text{wt \% primary intermediate})_n}{\text{molecular weight primary intermediate}_n}$$

Wherein the wt % of the primary intermediate refers to the level in the final composition, the molecular weight refers to the primary intermediate used and when multiple primary intermediates are used, the suffix in refers to each primary intermediate within the composition.

Surfactants

The composition of the invention comprises at least one surfactant. A surfactant can help to provide an emulsion.

The composition of the invention may comprise from 0.1% to 20%, preferably from 0.1% to 15%, more preferably from 0.2% to 12%, even more preferably from 0.5% to 10% of surfactants by total weight of the composition.

Preferably, the composition of the invention comprises one or more surfactants selected from the group consisting of anionic surfactants, non-ionic surfactants, amphoteric surfactants, zwitterionic surfactants, cationic surfactants, and mixtures thereof.

The one or more surfactants of the composition can be useful for stabilising a hydrophobic phase in the composition, e.g. for stabilising the gel network and/or lamellar structure.

The composition of the invention may comprise an anionic surfactant. The anionic surfactants may be selected from the group consisting of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants may be selected from the group consisting of sodium laurylethersulfate, sodium laurethethersulfate, sodium dodecyl sulfate, ammonium laurethethersulfate, ammonium dodecyl sulfate, alkylbenzenesulfonate, and combinations thereof.

The one or more surfactants of the composition of the invention may be non-ionic surfactants. The non-ionic surfactant(s) may be selected from the group consisting of lanolin alcohol, and polyoxyethylene ethers of fatly alcohols, and mixtures thereof. The non-ionic surfactant may be preferably ceteareth-n, wherein n is from 2 to 100, or from 10 to 30. When the one or more surfactants of the composition are non-ionic, precipitation of others ingredients of the composition can be prevented. Suitable nonionic surfactants are compounds that are well known (see, for example, in this respect "Handbook of Surfactants" by M. R. Porter, published by Blackie & Son (Glasgow and London), 1991, pp. 116-178).

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, such as POE/POP/POE (INCI: Poloxamer 184) (Trade Name: Pluracare L64, BASF), preferably oxyethylene units.

Examples of oxyalkylenated nonionic surfactants include:
oxyalkylenated ($C_8$-$C_{24}$)alkylphenols,
saturated or unsaturated, linear or branched, oxylalkylenated $C_8$-$C_{30}$ alcohols such as oxyethylenated cetylstearyl alcohol (33OE) or oleyl alcohol (10OE),
saturated or unsaturated, linear or branched, oxylalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, and mixtures thereof.

These surfactants contain a number of moles of ethylene oxide and/or of propylene oxide of between 1 and 100 and preferably between 2 and 50. Advantageously, the nonionic surfactants do not comprise any oxypropylene units.

Preferably, the oxyalkylenated nonionic surfactants are chosen from oxyethylenated $C_8$-$C_{30}$ alcohols, and esters of $C_8$-$C_{30}$ acids and of polyethylene glycols.

As examples of monoglycerolated or polyglycerolated nonionic surfactants, monoglycerolated or polyglycerolated $C_8$-$C_{40}$ alcohols are preferably used. In particular, the monoglycerolated or polyglycerolated $C_8$-$C_{10}$ alcohols correspond to the following formula:

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Poll glyceryl-4 Laurel Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the monoglycerolated or polyglycerolated alcohols, it is more particularly preferred to use the $C_8$-$C_{10}$ alcohol containing 1 mol of glycerol, the $C_{10}$-$C_{12}$ alcohol containing 1 mol of glycerol and the $C_{12}$ alcohol containing 1.5 mol of glycerol.

Preferably, the non-ionic surfactants of the composition of the invention are selected from the group consisting of POE/POP/POE (INCI: Poloxamer 184), oxyethylenated $C_8$-$C_{30}$ alcohols such as oxyethylenated cetylstearyl alcohol (33OE) or oleyl alcohol (10OE), esters of $C_8$-$C_{30}$ acids and of polyethylene glycols, and mixtures thereof.

More preferably, the non-ionic surfactants of the composition of the invention are selected from the group consisting of POE/POP/POE (INCI: Poloxamer 184) or oxyethylenated $C_8$-$C_{30}$ alcohols, such as oxyethylenated cetylstearyl alcohol (33 OE) or oleyl alcohol (10OE) and mixtures thereof.

Preferably, the surfactants of the composition of the invention are selected from the group consisting of non-ionic surfactants, anionic surfactants and mixtures thereof, more preferably, the surfactants of the composition are non-ionic surfactants.

Thickeners

The composition of the invention may also comprise one or more thickeners.

These thickeners may be chosen from fatty acid amides (coconut acid diethanolamide or monoethanolamide, oxyethylenated alkyl ether carboxylic acid monoethanolamide), polymeric thickeners such as cellulose-based thickeners (hydroxyethyl cellulose, hydroxypropylcellulose, carboxymethylcellulose), guar gum and derivatives thereof (hydroxypropylguar), fumed silicas, and clays, especially bentonites and hectorites, and derivatives thereof.

The content of thickener(s), if they are present, usually ranges from 0.01% to 20% and preferably from 0.1% to 5% by total weight of the composition.

The clay may be organically modified clay mineral. The organically modified clay mineral is used as an emulsion aid. The organically modified clay mineral is a type of colloidal aluminum silicate hydrate that has a three-layer structure that is prepared by modifying a clay mineral with a quaternary ammonium salt cationic surfactant. For example, organically modified bentonite and organically modified hectorite can be used.

Specific examples include dimethyldistearyl ammonium hectorite, dimethyl alkyl ammonium hectorite, benzyl dimethyl stearyl ammonium hectorite, and aluminum magnesium silicate treated with distearyl dimethyl ammonium chloride.

Preferably, the thickener are clays such as dimethyldistearyl ammonium hectorite.

Preferably, the thickener used in the composition of the invention is dimethyldistearyl ammonium hectorite.

Chelants

The composition of the invention may further comprise one or more chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in AE Martell & RM Smith, Critical Stability Constants, Vol. 1, Plenum Press, New York & London (1974) and AE Martell & RD Hancock, Metal Complexes in Aqueous Solution, Plenum Press, New York & London (1996), both incorporated herein by reference.

The composition of the invention may comprise a total amount of chelants ranging from at least 0.01%, preferably from 0.01% to 5%, more preferably from 0.1% to 3%, even more preferably from 0.25% to 1%, by total weight of the composition.

The one or more chelants may be selected from the group consisting of carboxylic acids (such as aminocarboxylic acids), phosphonic acids (such as aminophosphonic acids), polyphosphoric acids (such as linear polyphosphoric acids), their salts thereof and mixtures thereof.

By "salts thereof", it is meant in the context of chelants all salts comprising the same functional structure as the chelant they are referring to and including alkali metal salts, alkaline earth salts, ammonium salts, substituted ammonium salts, and mixtures thereof; alternatively sodium salts, potassium salts, calcium salts, magnesium salts, ammonium salts, and mixtures thereof; alternatively monoethanolammonium salts, diethanolammonium salts, triethanolammonium salts, and mixtures thereof.

The one or more chelants may be one or more aminocarboxylic acid chelants comprising one or more carboxylic acid moieties (—COOH) and one or more nitrogen atoms. The one or more aminocarboxylic acid chelants may be selected from the group consisting of diethylenetriamine pentaacetic acid (DTPA), diethylenetriamine-N,N',N"-polyacids, ethylenediamine disuccinic acid (EDDS), ethylenediamine-N,N'-diglutaric acid (EDDG), 2-hydroxypropylene-diatnine-N—N'-disuccinic acid (HPDDS), glycinamide-N, N'-disuccinic acid (GADS), ethylenediamine-N,N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), ethylene diamine tri(methylene phosphonate), hexamethylene diamine tetra (methylene phosphonate), their salts thereof, and mixtures thereof.

Alternatively, the one or more aminocarboxylic acid chelants may be selected from the group consisting of iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, dipicolinic acid, 2-phosphonobutane-1,2,4-tricarboxylic acid their salts thereof, their derivatives thereof, and mixtures thereof.

The one or more chelants may be one or more aminophosphonic acid chelants comprising an aminophosphonic acid moiety (—$PO_3H_2$) or its derivative —$PO_3R_2$, wherein $R_2$ is a $C_1$ to $C_6$ alkyl or aryl radical and salts thereof.

The one or more aminophosphonic acid chelants may be selected from the group consisting of aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof, alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

Other various chelants may also be contemplated, including the amino phosphonates, available as Dequest® from Monsanto, the nitriloacetates, the hydroxyethyl-ethylene triamines and the like which are known for such use. Suitable chelants for use herein may include organic phosphonates, such as the amino alkylene poly (aklene phosphonates), alkali metal ethane 1-hydroxy disphosphonates and nitrilo trimethylene phosphonates.

Preferably, the composition of the invention comprises a chelant selected from the group consisting of diethylenetri-amine-N,N',N"-polyacids, diethylenetriaminepentaacetic acid (DTPA), diethylenetriaminepenta(methylene phosphoric acid) (DTPMP), ethylene diamine tri(methylene phosphonate), hexamethylene diamine tetra (methylene phosphonate), ethylenediaminedisuccinic acid (EDDS), their salts thereof, their derivatives thereof, and mixtures thereof.

Organic Solvents

The composition of the invention may further comprise one or more organic solvents.

The one or more organic solvents may be selected to dissolve the compounds that would not typically be sufficiently soluble in water.

Suitable organic solvents include, but are not limited to: $C_1$ to $C_4$ lower alkanols such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol, monoethyl ether, monomethyl ether, hexylene glycol, glycerol, ethoxy glycol, butoxydiglycol, ethoxydiglycerol, dipropyleneglycol, polyglycerol); propylene carbonate; and mixtures thereof.

Preferably, the one or more solvents are selected from the group consisting of ethanol, propanol, isopropanol, glycerol, propylene glycol, hexylene glycol, dipropyleneglycol, propylene carbonate, and mixtures thereof.

The composition of the invention may comprise a total amount of organic solvents ranging from 0.11% to 20% by weight, preferably from 1% to 10% by weight relative to the total weight of the composition.

Water

According to the invention, the composition may comprise an amount of water greater than 2% by weight, preferably greater than 5% by weight relative to the total weight of the composition.

The composition of the invention may comprise less than 80% by weight of water, preferably less than 50% by weight of water, preferably between 5% and 50% by weight of water relative to the total weight of the composition.

pH Modifiers

According to the invention, the composition may further comprise a pH modifier in an amount that is sufficiently effective to adjust the pH of the composition to fall within a range prescribed above.

Suitable pH modifiers for use herein may include, but are not limited to ammonia, acidulents (such as inorganic and inorganic acids including for example phosphoric acid, acetic acid, ascorbic acid, citric acid or tartaric acid, hydrochloric acid); alkanolamines (such as monoethanolamine, diethanolamine, triethanolamine, monopropanolamine, dipropanolamine, tripropanolamine, 2-amino-2-methyl-1-propanol, and 2-amino-2-hydroxymethyl-1,3,-propanediol); guanidium salts, alkali metal such as sodium hydroxide, tetrasodium pyrophosphate or ammonium hydroxides and carbonates; and mixtures thereof.

The pH of the composition according to the invention may be preferably from 3 to 12, more preferably from 5 to 11, even more preferably from 7 to 11.

Oxidizing Agent(s)

The composition according to the invention comprises at least one oxidizing agent.

As used herein, "water-soluble" means that in standard conditions at least 0.1 g, preferably 1 g, more preferably 10 g of the oxidizing agent can be dissolved in 1 litre of deionized water at 25° C.

Suitable water-soluble oxidizing agents include, but are not limited to: inorganic peroxygen materials capable of yielding hydrogen peroxide in an aqueous solution.

The one or more oxidizing agents are valuable for the initial solubilisation and decolorisation of the melanin (bleaching) and accelerate the oxidation of the oxidative dye precursors (oxidative dyeing) in the hair shaft.

Suitable water-soluble peroxygen oxidizing agents include, but are not limited to:

hydrogen peroxide; inorganic alkali metal peroxides (such as sodium periodate and sodium peroxide); alkali metal bromates or ferricyanides, organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated, for example as monohydrates, tetrahydrates. Alkyl/aryl peroxides and/or peroxidases may also be used.

The percarbonates may be used to provide a source of both oxidizing agent and carbonate ions and or ammonium ions.

The oxidizing agent(s) may preferably be selected from the group consisting of hydrogen peroxide, urea peroxide and their salts thereof, and inorganic perhydrate salts, for instance alkali metals or alkaline-earth metals salts, such as sodium, potassium or magnesium, of persulfates, perborates and percarbonates, and mixtures thereof.

More preferably, the composition of the invention comprises an oxidizing agent selected from the group consisting of hydrogen peroxide, percarbonates, persulphates, and mixtures thereof.

The particularly preferred oxidizing agent is hydrogen peroxide.

A composition of the invention for lightening keratin fibers has a concentration of oxidizing agent in the composition from 1.5% to 2.5% by weight relative to the total weight of the composition. The concentration of oxidizing agent in the composition may be from 1.5% to 2.3% by weight, preferably from 1.5% to 2.2% by weight relative to the total weight of the composition.

Alternatively, the total amount of oxidizing agents in the composition may be at least 1.5% and not more than 2.3% by weight, alternatively not more than 2.2% by weight, alternatively not more than 2.1% by weight relative to the total weight of composition.

This composition can achieve the desired hair lightening while limiting the degradation of the keratin fibers.

A second composition of the invention for dyeing keratin fibers comprises:
- at least 20% by weight of fatty substances free of carboxylic acid groups relative to the total weight of the composition,
- at least one alkalizing agent,
- at least one surfactant,
- at least two oxidative dye precursors comprising one or more primary intermediates and one or more couplers, and
- at least one oxidizing agent, wherein the concentration of oxidizing agent in the composition is from 1.5% to 2.5% by weight relative to the total weight of the composition, wherein the total concentration of primary intermediates in the composition is more than 10 mM/kg of the composition. The color result of the composition has an L* value of less than 40 on natural white hair according to the L*a*b system.

More specifically, the color result of these compositions on natural white hair tray be brown/dark permanent hair color.

This composition may comprise a total amount of oxidative dye precursors ranging from 0.2% to 12%, preferably from 0.4% to 10%, more preferably from 0.5% to 8%, even more preferably from 0.5% to 6%, by total weight of the composition.

Such composition can achieve the desired hair lightening, i.e. deliver brown/dark permanent hair colors, with a low concentration of oxidizing agent. Such composition also presents low damages on the keratin fibers.

A third composition of the invention for dyeing keratin fibers comprises:
- at least 20% by weight of fatty substances free of carboxylic acid groups relative to the total weight of the composition,
- at least one alkalizing agent,
- at least one surfactant,
- at least two oxidative dye precursors comprising one or more primary intermediates and one or more couplers, and
- at least one oxidizing agent, wherein the concentration of oxidizing agent in the composition is from 2.6% to 4% by weight relative to the total weight of the composition and wherein the total concentration of primary intermediates in the composition is equal to or less than 10 mM/kg of the composition. The color result of the composition has an L* value greater than or equal to 40 on natural white hair according to the L*a*b system.

The concentration of oxidizing agent in this composition may be from 2.7% to 3.9%, preferably from 2.9% to 3.8% by weight relative to the total weight of the composition.

The total amount of oxidizing agents in this composition may be at least 2.6% and not more than 3.9% by weight, alternatively not more than 3.8% by weight, alternatively not more than 3.7% by weight relative to the total weight of composition.

More specifically, the color result of this composition on natural white hair may be blonde permanent hair color.

This composition may comprise a total amount of oxidative dye precursors ranging from 0.001% to 3%, preferably from 0.005% to 2.5%, more preferably from 0.008% to 2%, even more preferably from 0.01% to 1.5%, by total weight of the composition.

This composition can achieve the desired hair lightening, i.e. deliver blonde permanent hair colors, with a low concentration of oxidizing agent. This third composition also presents low damages on the keratin fibers.

Conditioning Agents

The composition according to the invention may further comprise at least one conditioning agent.

Typically, the composition may comprise a total amount of conditioning agents ranging from 0.05% to 10%, preferably from 0.1% to 8%, more preferably from 0.1% to 5%, even more preferably from 0.1% to 2% by total weight of the composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials, mineral oils and other oils such as glycerin and sorbitol and mixtures thereof.

The cationic polymers may be preferably selected from polymers of polyamine, polyamine amide and polyquaternary ammonium type, such as cyclopolymers of dialkdiallylamine or of dialkyldiallyammonium, including: dimethyldiallyammonium chloride polymers, such as polymers known as Polyquaternium-6.

Preferably, the conditioning agent is a cationic polymer chosen from the group of cyclopolymers of dialkyldiallylamine or of dialkyldiallyammonium, such as dimethyldiallyammonium chloride polymers.

Other Ingredients

According to the invention, the composition may comprise, in addition to the ingredients indicated above, further ingredients in order to further enhance the properties of the composition, as long as these are not excluded by the claims.

Suitable further ingredients include, but not limited to: anionic, cationic, nonionic, amphoteric or zwitterionic polymers or mixtures thereof, antioxidants, pigment, penetrating agents, sequestrants, perfumes, dispersing agents, film-forming agents, cosmetically acceptable carrier, radical scavengers, ceramides, preservatives, opacifying agents and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Method and Kits

A subject of the present invention is also a process for lightening or dyeing keratin fibers, comprising the application to the said keratin fibers of the composition as described above.

The composition of the invention may be obtained by mixing at least two or even three different compositions, or optionally more than three different compositions. One or more of the compositions may be anhydrous.

The expression "anhydrous compositions" is understood more particularly to mean compositions for which the water content is equal to 0 or less than 5% by weight, preferably less than 2% by weight and more particularly still less than 1% by weight, relative to the total weight of the composition.

Another subject of the invention relates to kit for lightening or dyeing keratin fibers comprising a first compartment containing a first composition comprising at least one fatty substance free of carboxylic acid groups, at least one alkalizing agent, optionally at least two oxidative dye precursors comprising one or more primary intermediates and one or more couplers, and in a second compartment, a second composition comprising at least one oxidizing agent. The compositions of the two compartments are intended to be mixed in order to provide the composition according to the invention, before application on keratin fibers.

Another subject of the invention relates to kit for lightening or dyeing keratin fibers comprising a first compartment containing a first composition comprising at least one fatty substance free of carboxylic acid groups, in a second compartment, a second composition comprising at least one alkalizing agent, optionally at least two oxidative dye precursors comprising one or more primary intermediates and one or more couplers, and in a third compartment, a third composition comprising at least one oxidizing agent. The compositions of the three compartments are intended to be mixed in order to provide the composition according to the invention, before application on keratin fibers.

The ingredients of the abovementioned compositions and the contents thereof are determined as a function of the characteristics detailed previously for the final composition according to the invention.

In each of the variants, the oxidizing composition is preferably an aqueous composition. In particular, it comprises more than 5% by weight of water, preferably more than 10% by weight of water and even more advantageously more than 20% by weight of water.

The pH of the oxidizing composition, when it is aqueous, is less than 7.

According to the invention, the composition applied to keratin fibers results from the mixing of two or more compositions, this mixing being performed either before application to keratin fibers or directly on the fibers without intermediate rinsing.

Thus, the composition of the invention may be applied to the wet or dry keratin fibers, successively and without intermediate rinsing.

The interval between the mixing of two or more compositions and the application of the mixture to the hair preferably does not exceed 30 minutes, preferably 10 minutes and even more preferably five minutes. The composition is applied to the hair at least 25 minutes, preferably at least 30 minutes more preferably at least 35 minutes.

The weight ratio of the amount of first composition used to the amount of the oxidizing composition may range from 0.2 to 3 and preferably from 0.3 to 1.

In addition, the composition according to the invention presents on the keratin fibers is left on for a time generally from about one minute to one hour and preferably from five minutes to 30 minutes.

The temperature during the process is, conventionally, preferably between room temperature (25° C.) and 80° C. and preferably between room temperature and 60° C.

After the treatment, the keratin fibers are optionally rinsed with water, optionally undergo washing with a shampoo followed by rinsing with water, and are then dried or left to dry.

The kits may also comprise as optional components a pre-treatment composition and/or a colour refresher composition. Such colour refresher compositions comprise at least one pre-formed dye and may be applied to the hair after the oxidative colour i.e. from about 1 minute after oxidative hair dye or bleach application to about 60 days after the application. These colour refresher composition can be used to increase the initial colour obtained and or boost the colour during the wash and style cycle until the next oxidative colouring event.

Test Method

Fourier Transform Infra-Red Analysis (FTIR Damage Test Method)

Fourier Transform Infrared (FTIR) analysis is a suitable method for quantifying the amount of cysteic acid produced from the oxidation of cystine during the dyeing/lightening process.

A Perkin-Elmer™ Spectrum Two FTIR equipped with a diamond Attenuated Total Internal Reflection (ATR) unit was used to measure the cysteic acid concentration in hair fibers. The nominal FTIR conditions utilized a spectral resolution of 4 $cm^{-1}$, a data interval of 0.7 $cm^{-1}$, a mirror scan speed of 0.2 cm $cm^{-1}$, and a scan range of 4,000 $cm^{-1}$ to 600 $cm^{-1}$. Prior to measuring the hair switch a background reading was made, Exemplary hair tresses were platted and were analyzed at four locations. The contact pressure used for assessing the switch was 120+/−3 cNm. The resulting sample spectra were then converted to an absorbance measurement and then normalized. Normalization is performed on the highest peak between 2000 and 1000 $cm^{-1}$ and on die 1450 $cm^{-1}$ peak. The highest peak is set to the value of 1.5, and the absorbance spectra scaled such that the 1450 $cm^{-1}$ peak has a value of 0. The normalized absorbance reading was then twice derivatized using a 13 points averaging system, and the minima of the second derivative of the absorbance at 1040 $cm^{-1}$ was taken as the as the relative concentration of cysteic acid. This yields a negative value, as would be expected due to the presence of a peak in the absorbance spectra and the double derivative process. To enable a more ready way to compare results, the value was scaled (multiplied by minus 10,000) to give a positive integer value for the amount of cysteic acid. Results were recorded as a calculated average of the four readings. This approach provides a relative scale of oxidative hair damage.

EXAMPLE

The following are non-limiting examples of the composition of the present invention. The examples are given solely for the purpose of illustration and are not to be construed as limitations of the present invention, as many variations thereof are possible without departing from the spirit and scope of the invention, which would be recognized by one of ordinary skill in the art.

The commercial names of the compounds presented in example 1 also apply for example 2.

"QS" or "QSP" means sufficient quantity for 100% or for 100 g

The first example corresponds to hair lightening compositions which do not contain any oxidative dyes.

The second example corresponds to hair dyeing composition containing oxidative dye precursors.

Example 1

The following lightening compositions are prepared (in the table below, the amounts are expressed in grams). The hair lightening composition according to the invention corresponds to composition A1.

1. Example A

| Composition A1 | Amount (% w/w) |
|---|---|
| Liquid petroleum jelly (Marcol 52, EXXON) | 55 |
| Octyldodecanol (Eutanol G, BASF) | 10 |
| Oleyl alcohol (10 OE) (Oleth-10, CRODA) | 5 |
| Disteasyldimethylammonium-modified hectorite (FRGEL200, HANGZHOU SINO-HOLDING CHEMICALS CO., LTD) | 1.5 |
| Ascorbic acid (OSKAR BERG GMBH) | 0.25 |
| Propylene carbonate (SIGMA ALDRICH) | 0.5 |
| Propylene glycol (BASF) | 2 |
| Ethanol (KWST) | 2.5 |
| Hexylene glycol (UNIVAR) | 1 |
| Dipropylene glycol (DOW) | 1 |
| Monoethanolamine (SASOL) | 4.5 |
| POE/POP/POE (Poloxamer 184) (Pluracare L64, BASF) | 9 |
| Diethylenetriaminepentaacetic acid (Diethylenetriamine-pentaacetic acid pentasodium salt solution, purum, 40% in H2O, SIGMA ALDRICH) | 1 |
| Demineralized water | Qs 100 |

The composition B1 is an oxidizing composition in accordance with the present invention.

The composition B2 is an oxidizing composition and corresponds to a comparative example.

| Composition (Amount % w/w) | Composition B1 | Composition B2 |
|---|---|---|
| Liquid petroleum jelly (Marcol 52, EXXON) | 20 | 20 |
| Cetearyl alcohol (BASF) | 8 | 8 |
| Oxyethylenated cetylstearyl alcohol (33 OE) (Simulsol CS Ecailles Ceteareth-33, SEPPIC) | 3 | 3 |
| Glycerol (SIGMA ALDRICH) | 0.5 | 0.5 |
| Hydrogen peroxide (50% Hydroxide peroxide Interox co-50, SOLVAY) | 6 | 12 |
| Sodium stannate (Sodium stannate trihydrate, 95%, SIGMA ALDRICH) | 0.04 | 0.04 |
| Tetrasodium pyrophosphate (Sodium pyrophosphate tetrabasic decahydrate, ACS reagent, ≥99%, SIGMA ALDRICH) | 0.03 | 0.03 |
| Polyquaternium-6 (40% Solution, Matrix Chemie (BASF)) | 0.2 | 0.2 |
| Vitamin E (BASF) | 0.10 | 0.10 |
| Phosphoric acid (Phosphoric acid solution, BIESTERFELD (BCD-CHEMIE)) | Qs pH 2.2 | Qs pH 2.2 |
| Demineralized water | Qs 100 | Qs 100 |

The level of hydrogen peroxide is subsequently described in active percent levels, which takes into account that a 50% solution is used within the formulations B1 and B2.

At the time of use, one part by weight of composition A1 is mixed with one part by weight of composition B1 and comprises 1.5% of hydrogen peroxide by weight compared to the weight of mixture.

One part by weight of composition A1 is also mixed with one part by weight of composition B2 and comprises 3.0% of hydrogen peroxide by weight compared to the weight of mixture.

The mixture is applied to tresses made of Level 5 (medium brown) hair (Kerling International Haarfabrik GmbH).

4 grams of the mixed composition is applied to each gram of tress, with the composition thoroughly worked into the tress. The tress is then placed into an oven at 30° C. for 35 min. Then, the tress is removed from the oven, rinsed with water for 2 min, washed twice with a standard shampoo and dried.

The color of the tresses is measured using a Minolta 2600d spectrophotometer. The color of the tress is measured at five points, on both the front and the back side of the hair tress. The 10 data points measured for each tress are converted into $L^*a^*b$ values assuming D65 lighting and a $10^0$ Observer.

The damages on the hair are also measured according to the FTIR test method.

Results Lightening:

|  | L* | a* | b |
|---|---|---|---|
| Untreated hair | 24.71 | 4.56 | 6.10 |
| Composition A1 + B1 | 30.55 | 7.92 | 12.68 |
| Composition A1 + B2 (comparative example) | 32.61 | 8.43 | 14.58 |

Results Damages on the Hair:

|  | FTIR values |
|---|---|
| Untreated hair | 28.56 |
| Composition A1 + B1 | 51.16 |
| Composition A1 + B2 (comparative example) | 58.20 |

2. Example B

The following lightening composition is prepared and corresponds to comparative example with a lower amount of fatty substance free of carboxylic acid groups (in the table below, the amounts are expressed in grams).

| Composition A2 (comparative example) | Amount (% w/w) |
|---|---|
| Cetearyl Alcohol (and) Dicetyl Phosphate (and) Ceteth-10 Phosphate (Crodafos CES, CRODA) | 10.00 |
| Cetearyl Alcohol (BASF) | 0.50 |
| Steareth-200 (Brij S200, CRODA) | 1.00 |
| Sodium Hydroxide Solution 50% | 0.14 |
| Xanthan Gum (JUNGBUNZLAUER AUSTRIA AG) | 0.05 |
| Propylene glycol (BASF) | 4.00 |
| Sodium sulfate Anhydrous (BCD CHEMIE) | 1.00 |
| Sodium sulphite (BCD CHEMIE) | 0.40 |
| Ascorbic acid (OSKAR BERG) | 0.30 |
| EDTA disodium salt (BASF) | 0.10 |
| Ammonium sulfate (BCD CHEMIE) | 1.00 |
| Trisodium Ethylenediamine Disuccinate (Innospec 30% active) | 3.35 |
| Diethylenetriamine Pentamethylene Phosphonic Acid | 0.21 |
| Monoethanolamine (SASOL) | 4.5 |
| Water Purified | QS 100 |

The composition B3 is an oxidizing composition,

| Composition Amount (% w/w) | Composition B3 |
|---|---|
| Cetearyl Alcohol (BASF | 3.40 |
| Ceteareth-25 (Cremopho A-25 BASF) | 0.80 |
| Salicylic acid (NOVACYL SAS) | 0.10 |
| Disodium Phosphate Anhydrous (BCD CHEMIE) | 0.08 |
| Phosphoric Acid (BCD CHEMIE) | QS to pH 2.2 |
| Etidronic Acid (UNIVAR LIMITED) | 0.01 |
| Hydrogen peroxide (50% Hydroxide peroxide Interox co-50, SOLVAY) | 12.00 |
| Water Purified | QS 100 |

The level of hydrogen peroxide is subsequently described in active percent levels, which takes into account that a 50% solution is used within the formulation B3.

At the time of use, one part by weight of composition A2 is mixed with one part by weight of composition B3 and comprises 3% of hydrogen peroxide by weight compared to the weight of mixture.

The same protocols of hair treatment and measurements have been performed as explained in example A.

Results Lightening:

|  | L* | a* | b |
|---|---|---|---|
| Untreated hair | 24.71 | 4.56 | 6.10 |
| Composition A2 + B3 | 30.20 | 7.66 | 12.14 |

Results Damages on the Hair:

|  | FTIR values |
|---|---|
| Untreated hair | 28.56 |
| Composition A2 + B3 | 52.25 |

3. Final Result

The following summarises the results of the hair lightening testing for compositions that will be compared for their ability to deliver brown/dark permanent hair color performance where it is important to provide some lightening, so as to enable blending the pigmented and grey hairs starting hair color, and hence provide good grey coverage.

|  | Amount of Hydrogen Peroxide in the mixture | Amount of Liquid Oil | L* | FTIR |
|---|---|---|---|---|
| Untreated hair | n/a | n/a | 24.71 | 28.56 |
| Composition A1 + B1 | 1.5% | >20% | 30.55 | 51.16 |
| Composition A2 + B3 (comparative example) | 3.0% | None | 30.20 | 52.25 |
| Composition A1 + B2 (comparative example) | 3.0% | >20% | 32.61 | 58.20 |

The brown/dark permanent hair lightening example (Composition A1+B1) of the invention provides:
  versus the comparative formulation without liquid oil with a regular level of hydrogen peroxide used for brown/dark shades (Composition A2+B3) significantly lower levels of damages as measured by FTIR test method and more lightening.
  versus the comparative high oil formulation with a regular level of hydrogen peroxide used for brown dark shades (Composition A1+B2) significantly lower levels of damages as measured by FTIR. Although there is a numerical difference in the lightness of these compositions, using the widely accepted approach of measuring color difference, using $dE_{2000}$ (weighting terms of L 2, C 1, H 1) (CIE. Improvement to industrial colour-difference evaluation. Vienna: CIE Publication No. 142-2001, Central Bureau of the CIE; 2001) the difference associated with L* is below 1.0. This by definition is not noticeable by the majority of observers. Therefore the difference in lightness is not consumer significant.

Only the inventive combination of A1+B1 is able to provide the required level of lightening at an acceptable level of damage for a permanent brown/dark shade. Thus, even if the concentration of oxidizing agent is decreased in the composition of our invention compare to comparative compositions (A1+B2 and A2+B3), the inventors have surprisingly found that with the composition according to the invention, the desired lightening on the hair is still obtained while the damage on the hair is decreased.

When the lightening composition A1+B1 comprises a concentration of oxidizing agent from 1.5% to 2.5% by weight relative to the total weight of the composition, we acknowledge that the composition according to the invention can achieve the same desired visual lightening as comparative compositions that comprises a higher concentration of oxidizing agent.

Example 2

The following dyeing compositions according to the invention are prepared (in the table below, the amounts are expressed in grams). The dyeing composition corresponds to compositions D (D1 to D5) and compositions E (E1 to E5).

1) Example of Blonde Dyeing Composition

Compositions D refer to examples of blonde dyeing composition.

| Composition D | D1 | D2 | D3 | D4 | D5 |
|---|---|---|---|---|---|
| Liquid petroleum jelly | 55 | 55 | 55 | 55 | 55 |
| Octyldodecanol | 10 | 10 | 10 | 10 | 10 |
| Oleyl alcohol (10 OE) | 5 | 5 | 5 | 5 | 5 |
| Distearyldimethylammonium-modified hectorite | 1.5 | 1.5 | 1.5 | 1.5 | 1.5 |
| Ascorbic acid | 0.25 | 0.25 | 0.25 | 0.25 | 0.25 |
| Propylene carbonate | 0.5 | 0.5 | 0.5 | 0.5 | 0.5 |
| Propylene glycol | 2 | 2 | 2 | 2 | 2 |
| Ethanol | 2.5 | 2.5 | 2.5 | 2.5 | 2.5 |
| Hexylene glycol | 1 | 1 | 1 | 1 | 1 |
| Dipropylene glycol | 1 | 1 | 1 | 1 | 1 |
| Monoethanolamine | 4.5 | 4.5 | 4.5 | 4.5 | 4.5 |
| POE/POP/POE (Poloxamer 184) | 9 | 9 | 9 | 9 | 9 |
| Diethylenetriaminepentaacetic acid | 1 | 1 | 1 | 1 | 1 |
| 2-methoxymethyl-p-phenylenediamine | | 0.050 | | | |
| toluene-2,5-diamine sulfate | 0.155 | | 0.018 | 0.063 | 0.376 |
| N,N-bis(2-hydroxyethyl)-p-phenylenediamine sulfate monohydrate | | | | 0.089 | |
| p-aminophenol | | 0.036 | 0.037 | | |
| resorcinol | 0.040 | 0.060 | 0.020 | | 0.180 |
| Methyl resorcinol | 0.040 | | | 0.060 | |
| Aminohydroxytoluene | | 0.015 | | | |
| 2,4-diaminophenoxyethanol 2HCl | | | 0.030 | | |
| 2-methyl-5-hydroxyethylaminophenol | | | 0.020 | | |
| m-amninophenol | 0.002 | | | 0.010 | 0.008 |
| Demineralized water | Qs 100 | Qs 100 | Qs 100 | Qs 100 | Qs 100 |

The composition F1 is an oxidizing composition in accordance with the present invention wherein the concentration of oxidizing agent in the composition is from 2.6% to 4% by weight relative to the total weight of the composition.

| Composition F1 | Amount (% w/w) |
|---|---|
| Liquid petroleum jelly | 20 |
| Cetearyl alcohol | 8 |
| Oxyethylenated cetylstearyl alcohol (33 OE) | 3 |
| Glycerol | 0.5 |
| Hydrogen peroxide in 50% solution | 6 |
| Sodium stannate | 0.04 |
| Tetrasodium pyrophosphate | 0.03 |
| Polyquaternium-6 | 0.2 |
| Vitamin E | 0.10 |
| Phosphoric acid | Qs pH 2.2 |
| Demineralized water | Qs 100 |

At the time of use, one part by weight of compositions D1 to D5 are each mixed with one part by weight of composition F1.

The level of oxidative dye primary intermediates in each of the formulations is calculated.

| Composition E | D1 | D2 | D3 | D4 | D5 |
|---|---|---|---|---|---|
| mM primary intermediates/kg | 3.5 | 3.3 | 2.1 | 2.9 | 8.5 |

The mixture is applied to tresses made of natural white hair (Kerling International Haarfabrik GmbH, "Greifsträhnen remis aus weißen").

4 grams of the mixed composition is applied to each gram of tress, with the composition thoroughly worked into the tress. The tress is then placed into an oven at 30° C. for 35 min. Then, the tress is removed from the oven, rinsed with water for 2 min, washed twice with a standard shampoo and dried.

The tresses were then visually inspected.

Result:

Tresses which had been treated with the composition that was the mixture of F1 and D1 provided a light blonde result.

Tresses which had been treated with the composition that was the mixture of F1 and D2 provided a light reddish blonde result.

Tresses which had been treated with the composition that was the mixture of F1 and D3 provided a light violet blonde result.

Tresses which had been treated with the composition that was the mixture of F1 and D4 provided a light bluish blonde result.

Tresses which had been treated with the composition that was the mixture of F1 and D5 provided a darker blonde result.

Then, the color of the tresses is measured using a Minolta 2600d spectrophotometer. The color of the tresses is measured at five points, on both the front and the back side of the hair tress. The 10 data points measured for each tress are converted into L*a*b values assuming D65 lighting and a 10° Observer.

|  | L* | a* | b |
|---|---|---|---|
| Composition F1 + D1 | 59.10 | 3.96 | 19.35 |
| Composition F1 + D2 | 60.39 | 9.87 | 18.95 |
| Composition F1 + D3 | 58.74 | 8.55 | 13.39 |
| Composition F1 + D4 | 59.25 | 2.86 | 13.06 |
| Composition F1 + D5 | 46.12 | 3.70 | 16.24 |

The L* values on natural white hair of compositions according to the invention which comprises a concentration of oxidizing agent from 2.6% to 4% by weight relative to the total weight of the composition are greater than 40.

Thus, with a lower value of oxidizing agent in the composition according to the invention, the composition according to the invention is able to provide the desired lightening properties, i.e. the blonde permanent hair color.

2) Example of Brown/Dark Dyeing Composition

Compositions E refer to examples of brown/dark compositions.

| Composition E | E1 | E2 | E3 | E4 | E5 |
|---|---|---|---|---|---|
| Liquid petroleum jelly | 55 | 55 | 55 | 55 | 55 |
| Octyldodecanol | 10 | 10 | 10 | 10 | 10 |
| Oleyl alcohol (10 OE) | 5 | 5 | 5 | 5 | 5 |
| Distearyldimethylammonium-modified hectorite | 1.5 | 1.5 | 1.5 | 1.5 | 1.5 |
| Ascorbic acid | 0.25 | 0.25 | 0.25 | 0.25 | 0.25 |
| Propylene carbonate | 0.5 | 0.5 | 0.5 | 0.5 | 0.5 |
| Propylene glycol | 2 | 2 | 2 | 2 | 2 |
| Ethanol | 2.5 | 2.5 | 2.5 | 2.5 | 2.5 |
| Hexylene glycol | 1 | 1 | 1 | 1 | 1 |
| Dipropylene glycol | 1 | 1 | 1 | 1 | 1 |
| Monoethanolamine | 4.5 | 4.5 | 4.5 | 4.5 | 4.5 |
| POE/POP/POE (Poloxamer 184) | 9 | 9 | 9 | 9 | 9 |
| Diethylenetriaminepentaacetic acid | 1 | 1 | 1 | 1 | 1 |
| 2-methoxymethyl-p-phenylenediamine |  |  |  | 0.765 |  |
| toluene-2,5-diamine sulfate | 1.000 | 3.690 | 0.785 |  | 1.565 |
| N,N-bis(2-hydroxyethyl)-p-phenylenediamine sulfate monohydrate |  |  | 0.120 |  |  |
| p-aminophenol |  |  |  | 0.360 | 0.190 |
| resorcinol | 0.350 | 0.900 | 0.350 | 0.500 | 0.900 |
| Methyl resorcinol |  | 0.200 |  | 0.250 |  |
| Aminohydroxytoluene |  |  |  |  | 0.030 |
| 2,4-diaminophenoxyethanol 2HCl |  | 0.800 | 0.100 |  |  |
| 2-methyl-5-hydroxyethylaminophenol |  |  |  |  | 0.050 |
| m-aminophenol | 0.150 | 0.400 | 0.04 | 0.200 |  |
| Demineralized water | Qs 100 | Qs 100 | Qs 100 | Qs 100 | Qs 100 |

The composition F2 is an oxidizing composition in accordance with the present invention wherein the concentration of oxidizing agent in the composition is from 1.5% to 2.5% by weight relative to the total weight of the composition.

| Composition F2 | Amount (% w/w) |
|---|---|
| Liquid petroleum jelly | 20 |
| Cetearyl alcohol | 8 |
| Oxyethylenated cetylstearyl alcohol (33 OE) | 3 |
| Glycerol | 0.5 |
| Hydrogen peroxide in 50% solution | 3 |
| Sodium stannate | 0.04 |
| Tetrasodium pyrophosphate | 0.03 |
| Polyquaternium-6 | 0.2 |
| Vitamin E | 0.10 |
| Phosphoric acid | Qs pH 2.2 |
| Demineralized water | Qs 100 |

At the time of use, one part by weight of compositions E1-E5 are each mixed with one part by weight of composition F2. The level of oxidative dye primary intermediates in each of the formulations was calculated.

| Composition E | E1 | E2 | E3 | E4 | E5 |
|---|---|---|---|---|---|
| mM primary intermediates/kg | 22.7 | 83.8 | 19.7 | 41.2 | 44.2 |

The mixture is applied to tresses made of natural white hair (Kerling International Haarfabrik GmbH, "Greifsträhnen renis aus weißen").

4 grams of the mixed composition is applied to each gram of tress, with the composition thoroughly worked into the tress. The tress is then placed into an oven at 30° C. for 35 min. Then, the tress is removed from the oven, rinsed with water for 2 min, washed twice with a standard shampoo and dried.

The tresses were then visually inspected.
Result:
Tresses which has been treated with the mixture of compositions F2 and E1 provides a medium brown result.
Tresses which has been treated with the mixture of compositions F2 and E2 provides a dark color result.
Tresses which has been treated with the mixture of compositions F2 and E3 provides a medium ash brown result.
Tresses which has been treated with the mixture of compositions F2 and E4 provides a medium golden brown result.
Tresses which had been treated with the mixture of compositions F2 and E5 provides a medium warm brown result.

The color of the tresses is measured using a Minolta 2600d spectrophotometer. The color of tresses is measured at five points, on both the front and the back side of the hair tress. The 10 data points for each tress are converted into L*a*b values assuming D65 lighting and a 10° Observer and averaged

|  | L* | a* | b |
|---|---|---|---|
| Compositions F2 + E1 | 26.06 | 4.38 | 3.84 |
| Compositions F2 + E2 | 18.30 | 0.34 | −0.84 |
| Compositions F2 + E3 | 26.83 | 0.81 | 0.88 |
| Compositions F2 + E4 | 32.55 | 6.31 | 10.96 |
| Compositions F2 + E5 | 26.88 | 4.45 | 7.59 |

The L* values on natural white hair of compositions according to the invention which comprises a concentration of oxidizing agent from 1.3% to 2.5% by weight relative to the total weight of the composition are below 40.

Thus, with a lower value of oxidizing agent in the composition according to the invention, the composition according to the invention is able to provide the desired lightening properties i.e. the brown/dark permanent hair color.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. Composition for dyeing keratin fibers, consisting of:
   at least 40% by weight of fatty substances which are emulsions in water and free of carboxylic acid groups relative to the total weight of the composition;
   wherein the fatty substances free of carboxylic acid groups are selected from the group consisting of: liquid hydrocarbons, liquid fatty alcohols, and any mixture thereof, and
   wherein the composition is free of any fatty acid comprising a carboxylic acid group, any fatty substance comprising a COO group and any fatty substance having oxyalkylene units and/or glycerol units;
   at least one alkalizing agent, wherein the at least one alkalizing agent comprises monoethanolamine alone or in combination with other alkalizing agents;
   at least one surfactant,
   at least two oxidative dye precursors comprising one or more primary intermediates and one or more couplers wherein the oxidative dye precursors are aromatic diamines, amino phenols, aromatic diols and/or derivatives thereof wherein the precursors are un-neutralized and/or are cosmetically acceptable amine salts and/or aromatic phenol or diol salts,
   at least one oxidizing agent at a concentration of from 1.5% to 2.1% by weight by weight relative to the total weight of the composition,
   at least one chelant in a range of from about 0.01% to about 5% by weight of the total weight of the composition, wherein the at least chelant comprises aminocarboxylic acid comprising diethylenetriamine-N, N', N"-polyacids, ethylenediamine disuccinic acid (EDDS), ethylenediamine-N,N' diglutaric acid (EDDG), glycinamide-N,N'disuccinic acid (GADS), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfsuccinic acids) (DDS), N, N'-bis(2-hydroxybenzyl)ethylenediamine-N,N'diacetic acid (HBED), ethylene diamine tri(methylene phosphonate), hexamethylene diamine tetra(methylene phosphonate), polyethyleneimine, polyphosphoric acid, etidronic acid, methylglycine diacetic acid, N-(2-hydroxyethyl)iminodiacetic acid, minodisuccinnic acid, N, N-dicarboxymethyl-L-glutamic acid, N-Lauroyl-N, N', N" ethylenediamine diacetic acid, a salt thereof, or a mixture thereof, water at a wt % of less than 50 wt % relative to the total weight of the composition;

alcohol consisting of ethanol, propanol, isopropanol, propylene glycol, hexylene glycol, dipropylene glycol, propylene carbonate or any mixture thereof; and, at least one or more of a pH modifier, a thickener, a conditioning agent, an anionic polymer, a cationic polymer, a nonionic polymer, an amphoteric polymer, a zwitterionic polymer, an antioxidant, a penetrating agent, a pigment, a film forming agent, a sequestrant, a perfume, a dispersing agent, a radical scavenger, a ceramid, a preservative, an opacifying agent, and any combination thereof.

2. The composition according to claim 1 the oxidizing agent is selected from the group consisting of hydrogen peroxide, percarbonates, persulphates, and mixtures thereof.

3. The composition according to claim 1 wherein the primary intermediates are selected from the group consisting of toluene-2,5-diamine, 2-methoxymethyl-pphenylenediamine, N,N-bis(2-hydroxyethyl)-p-phenylenediamine, p-aminophenol and mixtures thereof.

4. The composition according to claim 1 wherein the couplers are selected from the group consisting of resorcinol, methyl-resorcinol, naphthol, m-aminophenol, 4-amino-2-hydroxytoluene, 2-methyl-5-hydroxyethylaminophenol, 2,4-diaminophenoxyethanol, 2-amino-4-hydroxyethylaminoanisole and mixtures thereof.

5. The composition according to claim 1 wherein the surfactants are selected from the group consisting of non-ionic surfactants, anionic surfactants and mixtures thereof, preferably, non-ionic surfactants.

6. Process for lightening or dyeing keratin fibers wherein the composition according to claim 1 is applied to the keratin fibers.

7. The composition of claim 1, wherein the at least one chelant is in a range of from about 0.1% to about 3% by weight of the total weight of the composition.

8. The composition of claim 1, wherein the at least one chelant is in a range of from about 0.25% to about 1% by weight of the total weight of the composition.

9. The composition of claim 1, wherein the at least one chelant further comprises a carboxylic acid, a phosphonic acid, a polyphosphoric acid, a salt thereof, or a mixture thereof.

* * * * *